(12) United States Patent
Koch

(10) Patent No.: US 10,188,879 B2
(45) Date of Patent: *Jan. 29, 2019

(54) BREATHING CIRCUIT DEVICE

(71) Applicant: Dräger Safety AG & Co. KGaA, Lübeck (DE)

(72) Inventor: Jochim Koch, Ratzeburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 218 days.

This patent is subject to a terminal disclaimer.

(21) Appl. No.: 14/379,542

(22) PCT Filed: Feb. 27, 2013

(86) PCT No.: PCT/EP2013/053979
§ 371 (c)(1),
(2) Date: Aug. 19, 2014

(87) PCT Pub. No.: WO2013/127886
PCT Pub. Date: Sep. 6, 2013

(65) Prior Publication Data
US 2015/0007820 A1    Jan. 8, 2015

(30) Foreign Application Priority Data
Mar. 1, 2012    (DE) .......................... 10 2012 004 205

(51) Int. Cl.
*A62B 9/00*  (2006.01)
*A62B 19/00*  (2006.01)
(Continued)

(52) U.S. Cl.
CPC ......... *A62B 9/003* (2013.01); *A61M 16/1075* (2013.01); *A61M 16/22* (2013.01);
(Continued)

(58) Field of Classification Search
CPC ........... A62B 9/003; A62B 7/00; A62B 19/00; A61M 16/1075; A61M 16/22;
(Continued)

(56) References Cited

U.S. PATENT DOCUMENTS 4,168,706 A * 9/1979 Fletcher .................. A62B 7/10
128/204.16
4,586,500 A * 5/1986 Glynn .................... A62B 9/003
128/204.15

(Continued)

FOREIGN PATENT DOCUMENTS

DE    879 651 C    6/1953
DE    928 690 C    6/1955
(Continued)

*Primary Examiner* — Gregory Anderson
*Assistant Examiner* — Jonathan Paciorek
(74) *Attorney, Agent, or Firm* — McGlew and Tuttle, P.C.

(57) ABSTRACT

The invention relates to a respiratory circuit appliance with a respiratory line, a $CO_2$ absorber (6) in the respiratory line, and a cooling device for cooling the respiratory gas after it exits the $CO_2$ absorber. Provision is made that the cooling device cools a heating pump with a compressor (33) for compressing/condensing a cooling medium, a condenser (30), which receives the condensed cooling medium, and in so doing releases heat to the surroundings, and with a heat exchanger body (8) which receives the cooled cooling medium and is in heat-conducting contact with a section of the respiratory line.

18 Claims, 1 Drawing Sheet

(51) Int. Cl.
*A61M 16/10* (2006.01)
*A61M 16/22* (2006.01)
*A62B 7/00* (2006.01)

(52) U.S. Cl.
CPC ............... *A62B 7/00* (2013.01); *A62B 19/00* (2013.01); *A61M 2205/3368* (2013.01); *A61M 2205/3606* (2013.01); *A61M 2205/366* (2013.01)

(58) Field of Classification Search
CPC .. A61M 2205/3368; A61M 2205/3606; A61M 205/366
See application file for complete search history.

(56) References Cited

U.S. PATENT DOCUMENTS

| | | | |
|---|---|---|---|
| 5,269,293 A | 12/1993 | Löser et al. | |
| 5,435,152 A * | 7/1995 | McCausland | F04B 43/043 417/413.1 |
| 5,761,909 A * | 6/1998 | Hughes | F25B 21/02 165/DIG. 9 |
| 6,367,472 B1 * | 4/2002 | Koch | A61M 16/1075 128/203.12 |
| 6,990,979 B2 * | 1/2006 | Koch | A62B 7/08 128/204.13 |
| 7,410,291 B2 * | 8/2008 | Koch | G01K 1/20 374/102 |
| 2007/0125376 A1* | 6/2007 | Reinstadtler | A61M 16/1075 128/203.26 |
| 2010/0108063 A1* | 5/2010 | Koch | A61M 16/1075 128/204.15 |
| 2011/0247618 A1* | 10/2011 | Koch | A62B 7/00 128/204.15 |

FOREIGN PATENT DOCUMENTS

| | | |
|---|---|---|
| DE | 40 29 084 A1 | 3/1992 |
| DE | 10 2008 055700 A1 | 5/2010 |
| EP | 2 374 509 A1 | 10/2011 |

* cited by examiner

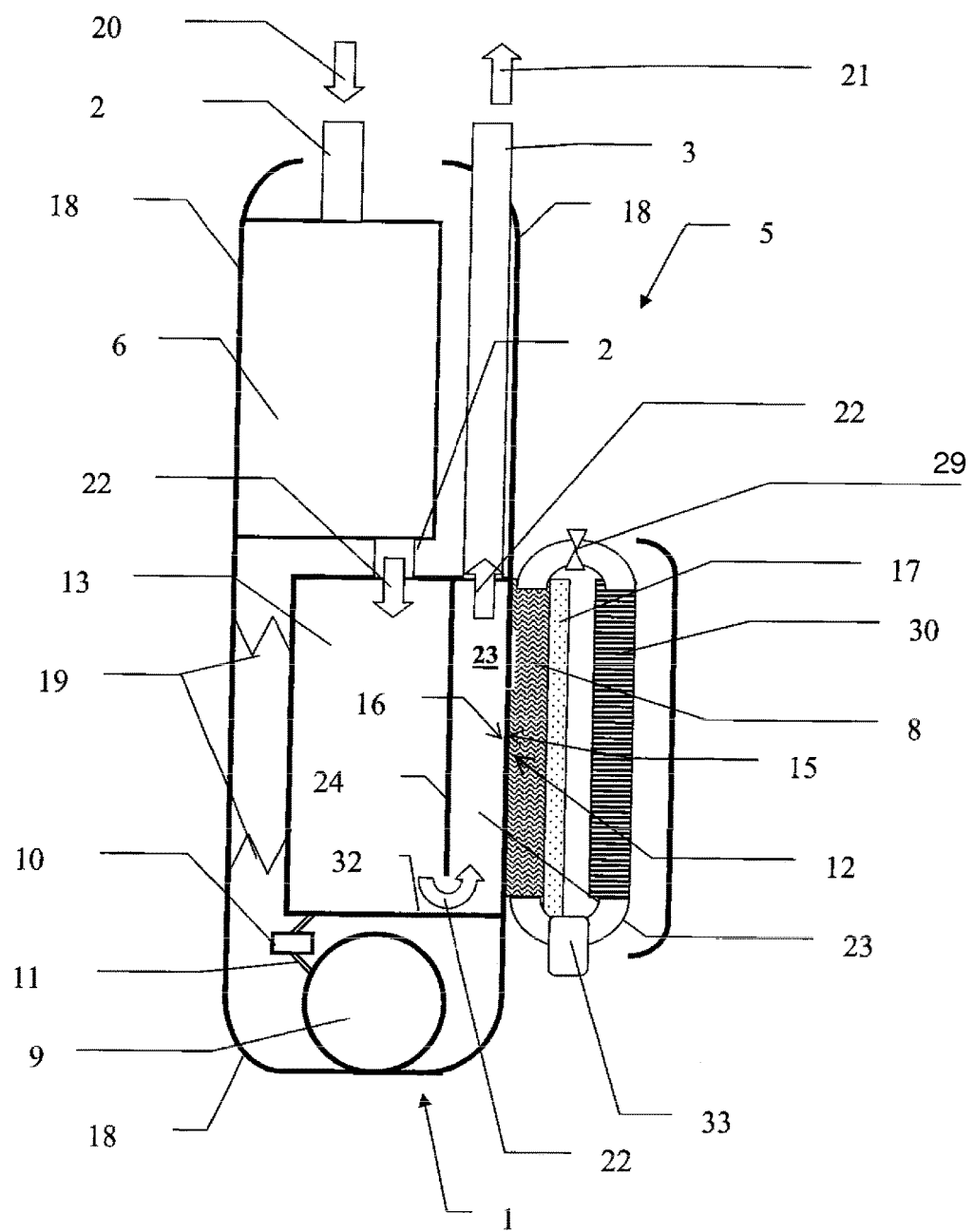

BREATHING CIRCUIT DEVICE

CROSS REFERENCE TO RELATED APPLICATIONS

This application is a U.S. National Phase Application of International Application PCT/EP2013/053979 filed Feb. 27, 2013 and claims the benefit of priority under 35 U.S.C. § 119 of German Patent Application DE 10 2012 004 205.1 filed Mar. 1, 2012, the entire contents of which are incorporated herein by reference.

FIELD OF THE INVENTION

The present invention pertains to a breathing circuit device with a breathing circuit line, a $CO_2$ absorber in the breathing circuit line and with a cooling means for cooling the breathing gas after it leaves the $CO_2$ absorber.

BACKGROUND OF THE INVENTION

The $CO_2$ generated by the user of the device and exhaled into the breathing circuit line must be absorbed in breathing circuit devices before the breathing gas is fed again to the user of the device. This is brought about by $CO_2$ absorbers in the breathing circuit line, which contain, in general, breathing lime or alkali. Moisture and heat (exothermal chemical reaction of the $CO_2$ with the absorber material) are formed in the $CO_2$ absorber due to the chemical reaction with the $CO_2$. This leads to a corresponding heating and humidification of the air to be inhaled again by the user of the device. The breathing air thus heated and humidified means a physiologically poorly tolerable breathing climate. Various methods have been developed in the state of the art to cool and dehumidify the breathing gas after the $CO_2$ absorber.

Ice is used for cooling in breathing circuit devices commonly used currently. This is complicated in respect to handling, because a block of ice must first be formed and then removed from the freezer shortly before the use of the breathing circuit device and inserted into the breathing circuit device. In addition, it is necessary for this to open the device.

As an alternative to the cooling by ice, a so-called regenerative cooler is also used for the commercially available breathing circuit devices, which uses instead of ice a latent heat storage medium, which makes the melting energy available for cooling. This concept is considerably simpler in terms of handling, because the cooler can be reused time and time again and is stored ready to use in the device. However, the cooling capacity is markedly lower because the PCM (phased change material) has a lower specific cooling capacity at equal volume and it is not possible to reach lower breathing gas temperatures due to the fact that the melting point of the PCM is above room temperature. Examples of such cooled breathing circuit devices are described in DE 879 651 and DE 928 690.

So-called zeolite coolers, which extract heat from the surrounding area by evaporating water and absorb the moisture in a zeolite, are known as another alternative for cooling in breathing circuit devices. Such a cooling means for cooling breathing gas in a breathing circuit device is known from DE 40 29 084 A1. However, the manufacture of such a reusable zeolite cooler is technically very complicated, because the zeolite must be stored under vacuum and tightness must be ensured for a very long time. In addition, the reusable cooler must be regenerated in a complicated manner. The zeolite must be dehumidified for this at temperatures above 200° C. and the water must be condensed in the evaporator. This is not practicable for use in respirators.

Further, zeolite coolers in a deformable packaging are known, which are deformable as cooling elements such that they can come into contact with the breathing circuit line after the $CO_2$ absorber in good heat-conducting contact, as is described in EP 2 374 509 A1. These may be manufactured, in principle, as disposable coolers, so that a complicated regeneration is avoided. However, this leads to a very high cost of use.

SUMMARY OF THE INVENTION

An object of the present invention is to provide a breathing circuit device with improved cooling and dehumidification of the breathing gas after discharge from the $CO_2$ absorber.

According to the invention, a breathing circuit device is provided with a breathing circuit line, a $CO_2$ absorber in the breathing circuit line and with a cooling means for cooling the breathing gas after it leaves the $CO_2$ absorber. The cooling means has a heat pump with a compressor for condensing a coolant and with a condenser, which receives the condensed coolant, cools the coolant and releases heat to the surrounding area in the process. A heat exchanger body receives the cooled coolant and is in heat-conducting (heat transferring) contact with a section of the breathing circuit line.

Provisions are made according to the present invention for the cooling means to have a heat pump, which cools, with a compressor for condensing a coolant, with a condenser, which receives the condensed coolant, and releases heat in the process to the surrounding area, and is provided with a heat exchanger body, which receives the cooled coolant and is in heat-conducting contact with the breathing circuit line.

The heat pump has a compressor, which is driven, for example, electrically and which condenses the coolant and heats same to about 40° C. to 75° C., depending on the dissipation of heat to the surrounding area. Due to the condensed coolant being passed on to a condenser, the coolant cools and condenses there. The condenser is in heat-exchanging connection with the surrounding area and can dissipate its heat there. The condenser can release its heat passively by convection and radiation; as an alternative, the convection may be intensified by the use of a small fan. The liquid coolant is passed on after the condenser to a heat exchanger body (evaporator), which is in thermal contact with the breathing gas to be cooled in the breathing circuit line. The cooled coolant has a very low temperature (for example, −10° C. to +10° C.). The heat exchanger in this case cools the breathing gas to a temperature of about 15° C. The coolant is evaporated in the process and is fed again to the compressor in a closed circuit.

The cooling means is provided in an advantageous embodiment with a fan, which generates an air stream for removing heat from the condenser.

The cooling means may be provided in an advantageous embodiment with air guiding means, which brings about a thermal convective flow, which is fed from the ambient air.

In an advantageous embodiment, the condenser is provided with cooling coils for releasing heat to the surrounding area.

In an advantageous embodiment, the heat exchanger body is in contact with a flexible breathing bag, which is part of the breathing circuit line, and the heat exchanger body is in contact with the side of the breathing bag along which the air leaving the breathing bag flows.

In an advantageous embodiment, the heat exchanger body is in heat-conducting contact with a solid, through the interior space of which, provided with a plurality of ribs, flows the breathing air that is to be cooled.

In a preferred embodiment, a control means is provided, which is set up to set the speed of the compressor to a preset value or to cycle the operating cycle times of the compressor such that the cooling output can be adapted to the cooling demand.

A temperature sensor may be preferably installed in the breathing circuit line. The temperature sensor reports (provides a signal as to) the breathing gas temperature and to the control means. The control means will then regulate the operation of the compressor such that a desired breathing gas temperature is detected by the temperature sensor.

The present invention will be described below on the basis of an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic sectional view of a breathing circuit device.

DESCRIPTION OF THE PREFERRED EMBODIMENTS

Referring to the drawings in particular, the breathing circuit device 1 according to the present invention shown in FIG. 1 has a breathing circuit line, in which the breathing gas of the user of the device circulates. FIG. 1 shows inlet line 2 for the exhaled breathing gas 20 leading into the cooling means 5 and the outlet line 3 from the cooling means 5. The breathing gas 20 exhaled by the user of the device enters a $CO_2$ absorber 6 through the inlet line 2. An exothermal chemical reaction, which removes $CO_2$ from the breathing gas, takes place in the $CO_2$ absorber 6. At the same time, the temperature and humidity of the purified breathing gas 22 leaving the $CO_2$ absorber 6 are increased. The breathing gas 22 then enters a breathing bag 13 and the breathing gas partially condenses on the colder wall of the bag and cools down in the process. The breathing gas 22 is deflected, as indicated by the arrow labeled 22, in the lower area of the breathing bag 13 and enters a small duct 23 which adjoins an inner wall 24 of the breathing bag and a flexible outer wall 16 of the breathing bag. To prevent the duct 23 from being able to be compressed, the duct is filled, for example, with a knitted fabric spacer (not shown). Via the outer wall 16, the duct 23 adjoins an evaporator 12, which has a lower temperature than the breathing gas. As a result, the temperature drops below the dew point of the saturated breathing gas and part of the moisture condenses on the wall 16. In addition, the breathing gas stream is cooled in the duct 23 by convection. The breathing gas 21 then leaves the outlet line 3 cooled and dehumidified and is fed to the user of the device for inhalation via the breathing circuit line.

A heat exchanger body 8 of the evaporator 12 is in contact with the duct 23 from the outside and is thermally insulated from the surrounding area by an insulation element 17 in order for the heat to be removed from the breathing circuit rather than from the surrounding area. Condensation on the side of the heat exchanger body 8 is also prevented thereby. The heat exchanger body 8 is connected with the condenser 30 via a flow resistance 29 and is supplied with liquid and cold coolant, which evaporates in the heat exchanger body 8 and cools the breathing circuit. The evaporated coolant is drawn in by the compressor 33, is compressed and the coolant temperature is markedly increased. The hot coolant is fed to the condenser 30 and is cooled there by the ambient air, while it condenses again.

The duct 23, through which the breathing gas flows in heat-conducting contact with the heat exchanger body 8, is pressed steadily towards the heat exchanger body 8, namely, towards the flexible wall 15 thereof by the inner overpressure relative to the surrounding area. Good heat transfer is generated thereby between the breathing gas flowing through the duct 23 and the heat exchanger body 8.

Springs 19, which ensure that the pressure in the breathing circuit is elevated relative to the surrounding area, are provided in the housing 18 of the breathing circuit device 1. The spring force is designed such that a minimum overpressure of, for example, 4 mbar is always present in the system. Further, an oxygen cylinder 9, from which oxygen is added to the breathing gas in the breathing bag 13 from line 11 via a valve 10, is provided in the housing 18 at the bottom.

The breathing circuit device 1 according to the present invention with an electrically operated heat pump has the advantage that the breathing gas can be cooled as needed. The heat pump needs to be turned on only when the breathing gas is heated and humidified by the absorber 6. The heat pump is able, for example, to cool the breathing gas to a temperature of 15° C., so that the moist component contains only about 11 g of water per kg of dry air. During a subsequent heating on its way to the user of the device, the breathing gas will then have a relative humidity of about 50%, which is precisely in the desired, physiologically comfortable range, at an outside temperature of 25° C.

The compressor 33 has, for example, an electric output of 75 W, i.e., it requires a current of approximately 3 A at 24 V. Under normal ambient temperature conditions, it reaches a cooling capacity of about 150 W in the breathing circuit. For use over 4 hours, the compressor 33 therefore requires a capacity of at least 12 ampere-hours. The weight of a commercially available battery that is suitable for this is about 1.8 kg. With all components, the cooling means weighs about 3 kg. This is about 1 kg higher than the weight of the ice cooler, but the cooling capacity is markedly higher in turn, it can be used as needed, and physiologically comfortable breathing conditions are obtained.

A breathing circuit device according to the present invention with heat pump cooling represents an improvement over prior-art cooling means, because handling is markedly improved and the cooling capacity can be regulated as desired. Cooling can be turned on as needed and is available without interruption as long as sufficient electric capacity is still present in the battery.

The cooling means described with heat pump may be designed as a complete module, which is attached to a correspondingly designed breathing circuit device as desired. The user can then use the cooling means with heat pump, PCM cooling or ice cooling depending on his needs, and a corresponding module must always be used as the cooling means.

It is assumed for considering the thermal balancing that the heat and moisture are produced predominantly in the breathing lime container of the $CO_2$ absorber 6. Breathing lime and the container are heated themselves and they release part of the heat in the form of convection and radiation to the surrounding area. The breathing bag 13 arranged downstream is heated by the breathing gas being discharged from the $CO_2$ absorber 6, from which $CO_2$ had been removed (to about 55° C. at an ambient temperature of 30° C.), and the humidity is saturated. The wall of the bag is heated hereby and it then releases heat to the surrounding area by radiation and convection. Since the humidity is saturated and the wall of the breathing bag is cooler, moisture condenses on the wall, and this moisture will accumulate in the breathing bag. If the use of this passive cooling effect of the breathing bag is to be continued, the active cooling means may only be arranged after the breathing bag proper.

Another advantage of the embodiment described is that the flexibility of the breathing bag 13, which includes or is provided with flexible wall 16 or includes the duct 23 with the flexible wall 16, and can be utilized to guarantee good heat transfer between the breathing gas to be cooled and the heat exchanger body 8. If the cooling means were in contact with a rigid, flat wall at the heat exchanger body 8, there would be design-related problems with heat transfer due to the poor agreement between the geometries and the insulating air inclusions and locally limited thermal contacts resulting therefrom. It must be assumed in case of the cooling elements known from the field of household appliances, which consist of simple plastic housings and are filled with a coolant (water, gel, PCM), that the surface is not flat. The cooling elements bulge somewhat out due to the increase in volume occurring during the phase transition between water and ice. The heat exchanger (evaporator) of the zeolite cooler sealed in films also fails to have a smooth, flat surface. Designing the breathing bag 13 as a flexible element (provided with flexible wall 16 or cooperating with the duct 23 with flexible wall 16) guarantees that the wall area of the breathing bag can adapt itself flexibly to the shape of the surface of the heat exchanger body of the heat pump in order to achieve the best possible heat exchange hereby.

Calculations and experience have shown that a contact area or exchange area of about 600 $cm^2$ to 900 $cm^2$ is necessary for the heat transfer. The intensive heat transfer is determined now predominantly by the heat of condensation on the wall rather than by the heat of convection, which itself has a poor heat transfer based on the flow velocity and the poor heat transfer coefficient of the flowing air. Therefore, the interposition of a thin flexible film is not relevant thermally.

While specific embodiments of the invention have been shown and described in detail to illustrate the application of the principles of the invention, it will be understood that the invention may be embodied otherwise without departing from such principles.

The invention claimed is:

1. A breathing circuit device comprising:
   a breathing circuit line;
   a carbon dioxide absorber in the breathing circuit line; and
   a cooling means for cooling the breathing gas after the breathing gas leaves the $CO_2$ absorber, the cooling means comprising a heat pump comprising:
      a compressor for condensing a coolant;
      a condenser, which receives the condensed coolant, cools the condensed coolant and releases heat to a surrounding area in the process; and
      a heat exchanger body, which receives the cooled coolant and is in heat-conducting contact with a section of the breathing circuit line, wherein the breathing line comprises a breathing bag, the breathing bag being a flexible element, wherein a wall area of the breathing bag adapts flexibly to a shape of a surface of the heat exchanger body of the heat pump.

2. A breathing circuit device in accordance with claim 1, wherein the cooling means further comprises a fan, which generates an air stream for removing heat from the condenser.

3. A breathing circuit device in accordance with claim 1, wherein the cooling means further comprises an air guide means for providing a thermal convective flow from the surrounding air.

4. A breathing circuit device in accordance with claim 1, wherein the condenser comprises cooling tubes, through which the coolant flows to release heat to the surrounding area.

5. A breathing circuit device in accordance with claim 1, wherein:
   the heat exchanger body is in contact with the flexible breathing bag;
   the heat exchanger body is in contact on the side of breathing bag along which air leaving the breathing bag flows.

6. A breathing circuit device in accordance with claim 1, further comprising:
   a control and analyzing unit; and
   a temperature sensor detecting a temperature in the breathing circuit line and connected with the control and analyzing unit, which controls the output of the heat pump to regulate the temperature in the breathing circuit line.

7. A breathing circuit device in accordance with claim 6, wherein the control and analyzing unit controls the operation of the heat pump either proportionally via speed or intermittently with a relative on time as a function of the measured temperature.

8. A breathing circuit device in accordance with claim 6, wherein the control and analyzing unit turns on the heat pump only when the temperature detected in the breathing circuit line exceeds a preset threshold.

9. A breathing circuit device in accordance with claim 7, wherein the control and analyzing unit turns on the heat pump only when the temperature detected in the breathing circuit line exceeds a preset threshold.

10. A breathing circuit device comprising:
    a breathing circuit line comprising at least one breathing passage from an inlet line to an outlet line;
    a carbon dioxide absorber connected to the breathing circuit line;
    a compressor for condensing a coolant;
    a condenser which receives the condensed coolant, cools the condensed coolant and releases heat to a surrounding area in the process; and
    a heat exchanger body, which receives the cooled coolant and is in heat-conducting contact with a section of the breathing circuit line, the breathing circuit line comprising a breathing bag, the breathing bag being a flexible element, wherein a wall area of the breathing bag adapts flexibly to a shape of a surface of the heat exchanger body.

11. A breathing circuit device in accordance with claim 10, further comprising a fan generating an air stream removing heat from the condenser.

12. A breathing circuit device in accordance with claim 10, further comprising an air guide defining a thermal convective flow path of surrounding air in a region at or adjacent to the condenser.

13. A breathing circuit device in accordance with claim 10, wherein the condenser comprises cooling tubes, through which the coolant flows to release heat to a surrounding area.

14. A breathing circuit device in accordance with claim 10, wherein:
   the heat exchanger body is in contact with the flexible breathing bag;
   the heat exchanger body is in contact on a side of the breathing bag along which air leaving the breathing bag flows.

15. A breathing circuit device in accordance with claim 10, further comprising:
   a temperature sensor detecting a temperature in the breathing circuit line and producing a signal indicative of the temperature; and
   a control and analyzing unit receiving the signal and controlling the compressor to regulate the temperature in the breathing circuit line.

16. A breathing circuit device in accordance with claim 15, wherein the control and analyzing unit controls the operation of the compressor by regulating a compressor speed or intermittently operating the compressor as a function of the measured temperature.

17. A breathing circuit device in accordance with claim 15, wherein the control and analyzing unit turns on the compressor only when the temperature detected in the breathing circuit line exceeds a preset threshold.

18. A breathing circuit device in accordance with claim 16, wherein the control and analyzing unit turns on the compressor only when the temperature detected in the breathing circuit line exceeds a preset threshold.

* * * * *